United States Patent
Wang et al.

(10) Patent No.: US 9,566,344 B2
(45) Date of Patent: Feb. 14, 2017

(54) DASATINIB AND NONLINEAR CONFIGURATION POLYETHYLENE GLYCOL CONJUGATE

(71) Applicant: JENKEM TECHNOLOGY CO., LTD.(TIANJIN), Tianjin (CN)

(72) Inventors: Jinliang Wang, Beijing (CN); Xuan Zhao, Beijing (CN); Zhenguo Wang, Beijing (CN)

(73) Assignee: Jenkem Technology Co., Ltd. (Tianjin), Tianjin (CN)

( * ) Notice: Subject to any disclaimer, the term of this patent is extended or adjusted under 35 U.S.C. 154(b) by 0 days.

(21) Appl. No.: 14/971,903

(22) Filed: Dec. 16, 2015

(65) Prior Publication Data

US 2016/0095934 A1    Apr. 7, 2016

Related U.S. Application Data

(63) Continuation of application No. PCT/CN2014/000599, filed on Jun. 18, 2014.

(30) Foreign Application Priority Data

Jun. 18, 2013    (CN) .......................... 2013 1 0241908

(51) Int. Cl.
  A61K 31/506    (2006.01)
  A61K 47/48     (2006.01)
  C07D 417/14    (2006.01)

(52) U.S. Cl.
  CPC ....... *A61K 47/48215* (2013.01); *A61K 31/506* (2013.01); *C07D 417/14* (2013.01)

(58) Field of Classification Search
  CPC .................................................. C07D 417/14
  See application file for complete search history.

(56) References Cited

U.S. PATENT DOCUMENTS

| | | | |
|---|---|---|---|
| 8,816,077 B2* | 8/2014 | Riggs-Sauthier | A61K 47/48215 544/295 |
| 8,959,984 B2* | 2/2015 | Daub ..................... | C12Q 1/485 210/656 |
| 9,108,954 B2* | 8/2015 | Yan ....................... | C07D 417/12 |
| 2012/0094998 A1* | 4/2012 | Riggs-Sauthier ........... | A61K 47/48215 514/234.8 |
| 2014/0194307 A1* | 7/2014 | Hitko .................. | G01N 33/502 506/9 |
| 2014/0194325 A1* | 7/2014 | Hitko .................. | G01N 33/542 506/18 |
| 2015/0087043 A1* | 3/2015 | Arnold ................. | C07D 417/14 435/184 |
| 2015/0152187 A1* | 6/2015 | Sun .................. | A61K 47/48638 530/391.1 |
| 2015/0359900 A1* | 12/2015 | Wang ............... | A61K 47/48246 514/1.6 |
| 2016/0082117 A1* | 3/2016 | Xu .................... | A61K 47/48215 514/252.02 |
| 2016/0193347 A1* | 7/2016 | Xu ...................... | C07D 417/12 514/1.3 |

FOREIGN PATENT DOCUMENTS

| CN | 102108119 A | 6/2011 |
|---|---|---|
| CN | 101385860 B | 11/2011 |

OTHER PUBLICATIONS

SIPO Office Action for CN104255611 (priority application), dated Apr. 5 2016.

* cited by examiner

*Primary Examiner* — Alexander R Pagano
(74) *Attorney, Agent, or Firm* — Zareefa B. Flener; Flener IP Law

(57) ABSTRACT

A dasatinib and nonlinear configuration polyethylene glycol conjugate represented by formula I, wherein core is the core structure of a nonlinear configuration of polyethylene glycol, selected from a residue of pentaerythritol, methylglucoside, sucrose, diethylene glycol, propanediol, glycerol or polyglycerol removaed the hydrogen atom from the hydroxyl group; P is a polyethylene glycol residue with a number-average molecular weight of 300-60000 Da; X is selected from single bond, —$CH_2CO$—, —$CH_2CH_2OCO$— or $CH_2CH_2NHCO$—; and i is selected from 3, 4, 6 or 8.

(I)

12 Claims, No Drawings

DASATINIB AND NONLINEAR CONFIGURATION POLYETHYLENE GLYCOL CONJUGATE

CROSS-REFERENCE TO RELATED APPLICATION

The application is a continuation of PCT/CN2014/000599 (filed on Jun. 18, 2014), which claims priority from CN Patent Application Serial No. 201310241908.7 (filed on Jun. 18, 2013), the entire contents of which are incorporated herein by reference for all purposes.

FIELD OF THE INVENTION

The present invention belongs to the field of medical technology, and relates to a dasatinib and nonlinear configuration polyethylene glycol conjugate, particularly a conjugate formed by dasatinib and polyethylene glycol with four branches and pharmaceutical compositions thereof.

BACKGROUND OF THE INVENTION

Chronic myelocytic leukemia (CIVIL) is a malignant neoplasm affecting the blood and bone marrow which may occur at all ages, and most patients are middle-aged or elderly people, and male patients are slightly more than female patients. In western populations, CIVIL patients account for 15%-20% of adult leukemia patients. According to the characters and research of clinical significance, CIVIL is usually divided into three categories. With the absence of intervention factors, CML usually starts from the "chronic phase", and after several years CML enters the "acceleration phase", and ultimately it goes into the "blast phase". Blast phase is the final phase of CML with a pathological condition similar to acute leukemia. If drug treatment is taken in time, this progressive process is usually stopped.

In the chronic phase of CML, imatinib (with a trade name of "Gleevec") is the preferred tyrosine kinase inhibitor. This drug was approved by the U.S. Food and Drug Administration (FDA) in 2001 and has been demonstrated to inhibit bone hyperplasia diseases (cytogenetic response) in vivo of majority of CML patients (65-75%). However, the mutation of BCR-ABL kinase domain in many tumor cells results in the imatinib resistance in many patients. Hence, a number of new products get promoted. One of them is called dasatinib (with a trade name of "Sprycel"), which can block multiple oncogenic proteins, and was approved by FDA to be applied for patients in all disease phases of CIVIL with previous treatment failure or intolerance, and also for the adult ALL patients who are Philadelphia chromosome-positive with resistant or intolerance to other therapies. The structure of dasatinib is shown as formula (XII):

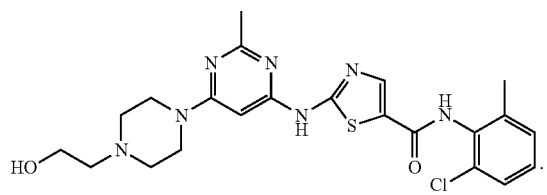

(XII)

Clinical trials show that the curative effect of dasatinib is better than that of imatinib with high dose, and no resistance of dasatinib is found, but in the process of application, there are still some adverse drug reactions, such as fever, pleural effusion, febrile neutropenia, gastrointestinal bleeding, pneumonia, thrombocytopenia, dyspnea, anemia, diarrhea and cardiac failure etc. In addition, FDA announced that dasatinib might increase the risk of pulmonary hypertension in October 2011, therefore, FDA decided to add this risk information into warnings and precautions in the drug instructions of Sprycel. Therefore, certain modifications of dasatinib and its derivatives may help to increase curative effect thereof and reduce possible toxic and side effects.

Polyethylene glycol (PEG) modification technology is a new drug administration technology which has developed rapidly in recent years and is mainly applied in the injection administration system. It is a technology linking activated polyethylene glycol to a drug molecule or its surface. Small molecule drugs, after being modified by polyethylene glycol, mainly have the following advantages: 1. increased water-solubility of drugs; 2. reduced toxicity; 3. prolonged cyclic half-life of drugs, reduced times of administration, improved patient compliance, improved life quality and reduced treatment fees; 4. reduced enzyme degradation and improved bioavailability; 5. decreased permeability of blood-brain barrier and reduced central side effects. After the drugs being linked with polyethylene glycol, pharmacokinetics of the drugs changes and thereby pharmacodynamics thereof changes. Especially polyethylene glycol could prolong the time for plasma concentration being maintained or close to the target concentration to make the drug efficacy to be fully realized. Additionally, the drugs linked with polyethylene glycol have a water-solubility which is greatly improved, and more importantly could achieve a purposes of "passive targeting" administration. The mechanism of passive targeting is determined by effective penetration of macromolecular prodrugs into the tumor tissues, and the penetration ability is closely associated with the molecule size and structure type of polyethylene glycol and other factors.

In the invention WO2010120387 disclosed, the modification of tyrosine kinase inhibitor class (Tinibs) of antitumor drugs by polyethylene glycol is adopted, but the molecule size and structure type of polyethylene glycol and other factors are not fully considered, and the polyethylene glycol molecules chosen in this invention are single-functional or double-functional linear configuration molecules. The obvious drawbacks of the modification of small molecule drugs by this kind of linear configuration polyethylene glycol are a small drug loading, a large proportion of inactive molecules, and problems in metabolism, clear of drugs and so on.

SUMMARY OF THE INVENTION

The present invention uses nonlinear configuration polyethylene glycol for the structural modification of dasatinib to increase the water-solubility of small molecule drug, and enable the small molecule drug to be developed into an injection or other suitable dosage forms.

The present invention provides a dasatinib and nonlinear configuration polyethylene glycol conjugate shown as formula I

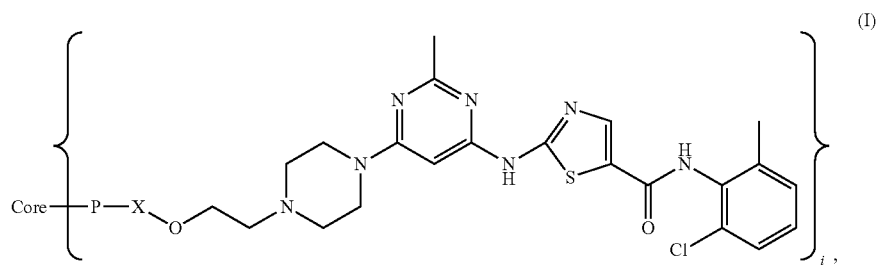

wherein Core is the core structure of the nonlinear configuration polyethylene glycol, selected from residues of pentaerythritol, methylglucoside, sucrose, diethylene glycol, propanediol, glycerol or polyglycerol removed a hydrogen atom from the hydroxyl group; P is a polyethylene glycol residue with a number-average molecular weight of 300-60000 Da; X is selected from a single bond, —CH$_2$CO—, —CH$_2$CH$_2$OCO— or —CH$_2$CH$_2$NHCO—; and i is selected from 3, 4, 6 or 8. In some embodiments, the conjugate described above is shown as formula II:

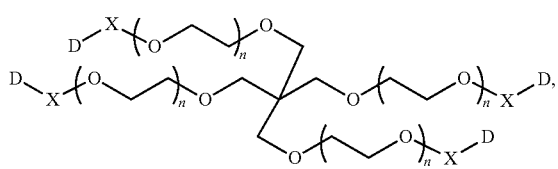

wherein n is an integer in a range of 30-200; X is selected from a single bond, —CH$_2$CO—, —CH$_2$CH$_2$OCO— or —CH$_2$CH$_2$NHCO—; D is the dasatinib residue shown as structure III:

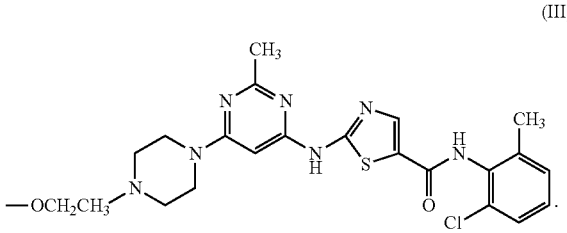

In some embodiments, the conjugate described above is shown as formula IV:

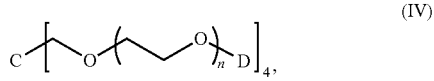

wherein n is an integer in a range of 30-200.

In some embodiments, the conjugate described above is shown as formula V:

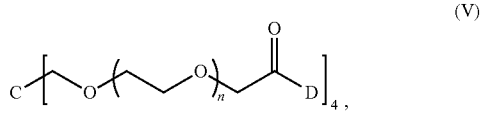

wherein n is an integer in a range of 30-200.

In some embodiments, the conjugate described above is shown as formula VI:

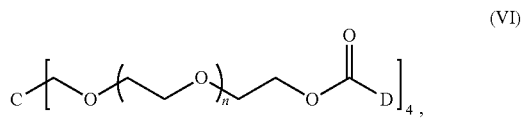

wherein n is an integer in a range of 30-200.

In some embodiments, the conjugate described above is shown as formula VII:

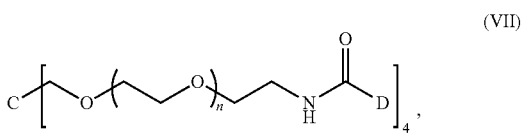

wherein n is an integer in a range of 30-200.

In some embodiments, the nonlinear configuration polyethylene glycol described above has a number-average molecular weight of 5000-40000 Da and four branches.

In some embodiments, the nonlinear configuration polyethylene glycol described above has a number-average molecular weight of 20000 Da and four branches.

In some embodiments, the conjugate described above is selected from the group consisting of conjugates as shown in formula VIII to formula XI:

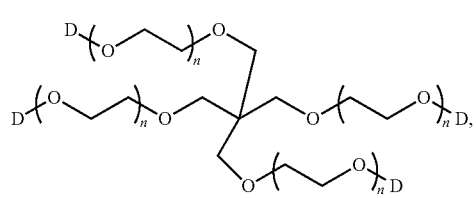

(IX)

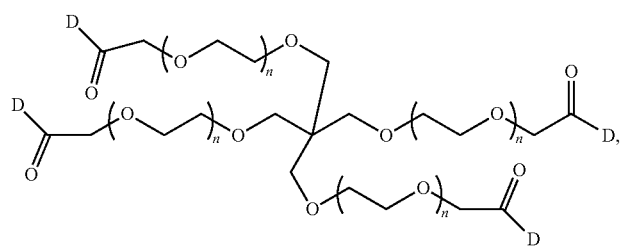

(X)

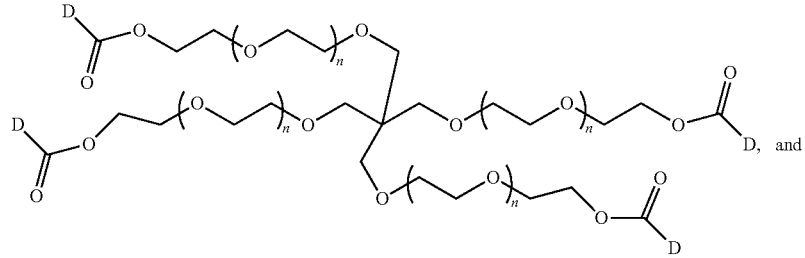
D, and (XI)

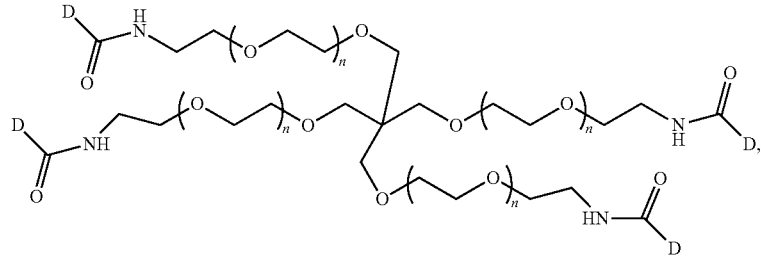

wherein n in formula (VIII) to formula (XI) is an integer in a range of 30-200.

The present invention also provides a pharmaceutical composition comprising the conjugate according to the present invention and pharmaceutically acceptable carriers or excipients.

In some embodiments, the pharmaceutical composition described above is selected from tablets, capsules, pills, granules, powders, suppositories, injections, solutions, suspensions, ointmens, patches, lotions, drops, linimentums, sprays or other dosage forms.

The present invention also provides the use of the conjugate according to the present invention in the preparation of antitumor drugs.

The present invention also provides a pharmaceutical composition comprising dasatinib and nonlinear configuration polyethylene glycol conjugate described above and pharmaceutically acceptable carriers or excipients.

In some embodiments of the present invention, the pharmaceutical composition described above is selected from tablets, capsules, pills, granules, powders, suppositories, injections, solutions, suspensions, ointments, patches, lotions, drops, linimentums, sprays and other dosage forms.

The present invention also provides the use of dasatinib and nonlinear configuration polyethylene glycol conjugate and pharmaceutical composition thereof in the preparation of antitumor drugs.

In the present invention, the modification by nonlinear configuration of polyethylene glycol may greatly improve the solubility of dasatinib, improve absorption of drugs, prolonged duration of drug function, enhance curative effect, and reduce toxic and side effects.

DETAILED DESCRIPTION OF THE INVENTION

In the structure of dasatinib there is a hydroxyl group, and introducing polyethylene glycol, especially nonlinear configuration polyethylene glycol, into the structure of dasatinib may realize the purpose of reducing hydrophobicity of dasatinib, increasing hydrophilicity of dasatinib, enhancing curative effect, and reducing toxic and side effects.

The conjugates according to the present invention may be administered in the form of pure compound or suitable pharmaceutical compositions with any acceptable drug delivery systems or regents for similar application. Thus, the conjugates according to the present invention may be administered orally, nasally, parenterally, topically, transdermally or rectally, in the form of solid, semi-solid or liquid medicaments, e.g., tablets, suppositories, pills, soft and hard gelatin capsules, powders, solutions, suspensions and injections etc, and the unit dosage forms which are suitable for precise and simple administration are preferred. The compositions may contain conventional pharmaceutical carriers or excipients and conjugates according to the present invention as active ingredients (one or more). In addition, it may include other medicaments, carrier and adjuvants etc.

Generally, according to the modes of administration required, the pharmaceutically acceptable compositions contain the conjugates according to the present invention with a weight percentage of about 1 to about 99 and suitable pharmaceutical excipients with a weight percentage of about 99 to 1. The compositions comprising conjugates according to the present invention with a weight percentage of about 5 to 75 and suitable pharmaceutical excipients are preferred.

The pharmaceutical compositions may be administered in liquid form, e.g. by dissolving or dispersing the conjugates according to the present invention (from about 0.5 to about 20%) and pharmaceutically acceptable adjuvants which are employed selectively into carriers to thereby form a solution or suspension, the examples of carrier are water, saline, glucose hydrate, glycerol and ethanol etc.

If necessary, the pharmaceutical compositions according to the present invention may also contain minor amounts of auxiliary substances such as wetting agents or emulsifiers, pH buffers, antioxidants etc, for example: citric acid, sorbitan monolaurate, triethanolamine oleate and butylated hydroxy toluene etc.

The following embodiments are the descriptions of the present invention, which cannot be used to limit the protection scope of the present invention.

EXAMPLES

The dasatinib used in the embodiments is provided by Xingcheng Chempharm Co., Ltd. in Taizhou, Zhejiang, the p-toluenesulfonyl chloride is purchased from Yilong Industrial Co., Ltd. in Shandong, sodium hydride is purchased from TCI (Shanghai) Development Co., Ltd., four branches polyethylene glycol, four branches polyethylene glycol acetic acid and four branches polyethylene glycol amine are provided by Jenkem Technology Co., Ltd. in Beijing, other reagents are commercially available.

Example 1

The Preparation of Compound DSN-01 ($^{20k}$4arm-PEG-OCH$_2$CH$_2$ODS)

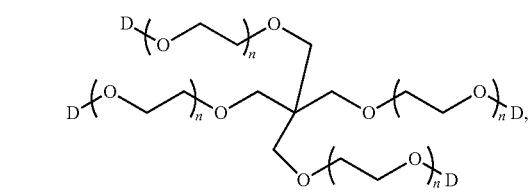

(DSN-01)

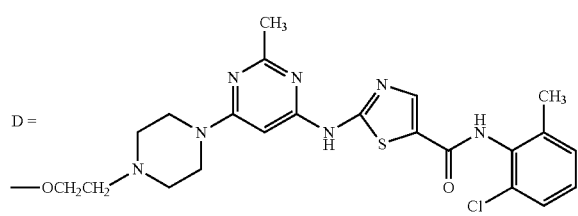

191 mg of p-toluenesulfonyl chloride and 2 mL of pyridine were added into the reaction flask, the mixture obtained was cooled after being stirred and dissolved, and to the reaction flask was added followed by the drop-wise addition of mixture of 2 g of the four branches polyethylene glycol (with a number-average molecular weight of 20000, 1 mmol) and 4 mL of pyridine, and the reaction was continued until it was complete, the solvent was evaporated under reduced pressure, and the residue obtained was crystallized by using isopropanol to give 1.8 g of whitish solid used directly in the next reaction.

To a mixture of 304 mg (0.4 mmol) of dasatinib in 30 mL of dimethylformamide (DMF) 48 mg of NaH was added and the mixture obtained was stirred at room temperature for 1 h, and then 1.8 g of four branches polyethylene glycol tosylate was added and then the reaction was kept at room temperature for 20 h. The solvent was evaporated under reduced pressure, and the residue obtained was crystallized by using isopropanol to give 1.6 g of white solid (i.e. DSN-01).

$^{13}$C-NMR (75 MHz, DMSO-d$_6$): 18.8, 25.7, 33.7, 41.2, 51.2, 55.2, 58.1, 66-73, 84.0, 126.5, 127.1, 128.8, 129.6, 133.0, 133.8, 139.4, 141.2, 157.5, 160.4, 162.1, 162.8, 165.7.

Example 2

The Preparation of Compound DSN-02 ($^{20k}$4arm-PEG-OCH$_2$COODS)

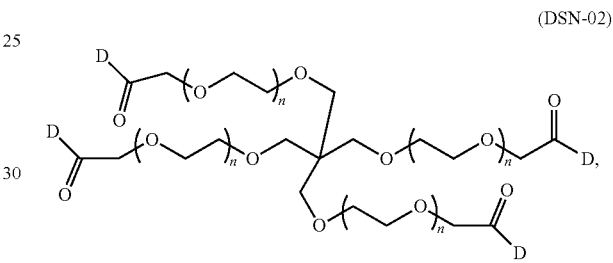

(DSN-02)

2 g of four branches polyethylene glycol acetic acid (with a number-average molecular weight of 20000, 1 mmol), 81.1 mg (0.6 mmol) of HOBt and 73.3 mg (0.6 mmol) of dimethylaminopyridine (DMAP) were added into the reaction flask, the mixture obtained was dissolved by dichloromethane, and then 75.9 mg (0.6 mmol) of dasatinib dissolved in DMF, 25.8 mg (0.8 mmol) of diisopropylethylamine (DIPEA) and 115 mg (0.6 mmol) of 1-(3-dimethylamino propyl)-3-ethylcarbodiimide hydrochloride (EDCI) were added into the reaction flask, after completion of the addition, the ice bath was removed and the reaction solution was allowed to rise to room temperature naturally, then the reaction was kept overnight, and then the solvent was evaporated under reduced pressure, the residue obtained was crystallized by using isopropanol to give 1.5 g of white solid (i.e. DSN-02).

$^{13}$C-NMR (75 MHz, DMSO-d$_6$) : 19.0, 25.9, 33.7, 41.5, 51.4, 55.6, 58.7, 66-73, 84.5, 127.2, 127.5, 129.3, 130.7, 133.8, 134.2, 140.5, 141.7, 158.1, 160.9, 162.4, 163.2, 166.2, 176.0.

Example 3

The Preparation of Compound DSN-03 ($^{20k}$4arm-PEG-OCH$_2$CH$_2$OCOODS)

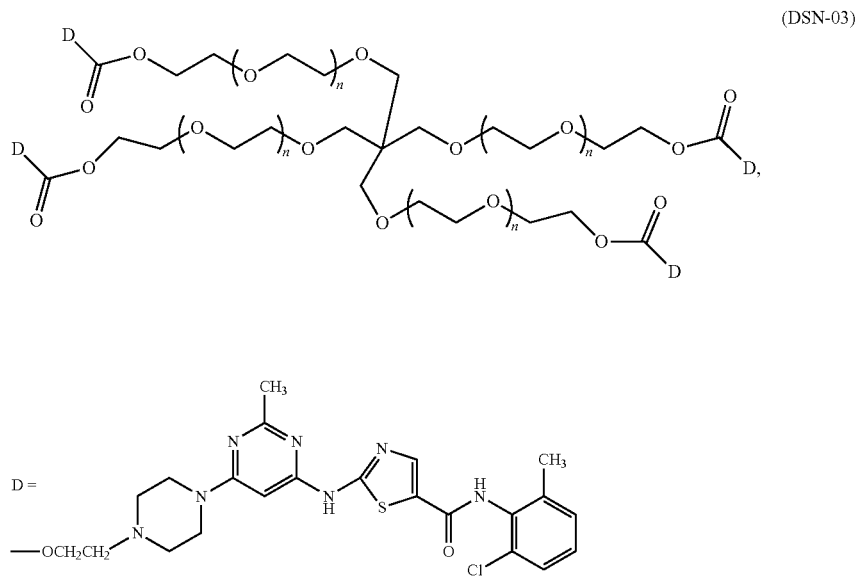

(DSN-03)

2 g of four branches polyethylene glycol (with a number-average molecular weight of 20000, 1 mmol) was added into the reaction flask and then dissolved by dichloromethane, then 64.8 mg (0.4 mmol) of N,N'-carbonyldiimidazole was added and the mixture was stirred at room temperature until the conversion of raw materials was complete. Then 75.9 mg (0.6 mmol) of dasatinib dissolved in DMF was added and the mixture obtained was heated to reflux until the completion of the reaction, the solvent was evaporated under reduced pressure, the residue obtained was crystallized by using isopropanol to give 1.7 g of white solid (i.e. DSN-03).

$^{13}$C-NMR (75 MHz, DMSO-d6): 18.9, 25.8, 33.7, 41.4, 51.3, 55.4, 58.5, 66-73, 84.1, 126.7, 127.3, 128.9, 129.7, 133.2, 133.9, 139.5, 141.3, 151.5, 157.6, 160.5, 162.4, 163.0, 165.9.

Example 4

The Preparation of Compound DSN-04 ($^{20k}$4arm-PEG-OCH$_2$CH$_2$NHCOODS)

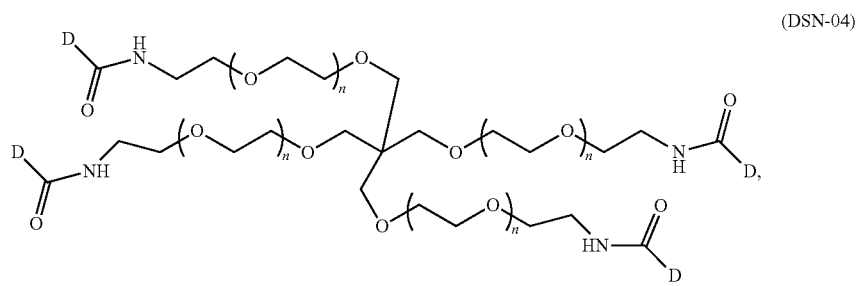

(DSN-04)

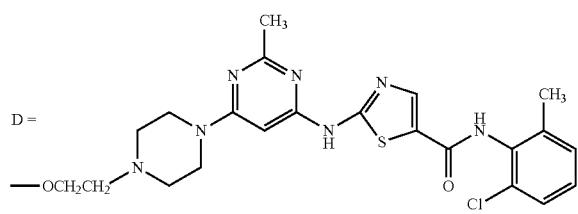

2 g of four branches polyethylene glycol amine (with a molecular weight of 20000, 1 mmol) was added into the reaction flask and then dissolved by dichloromethane, then 64.8 mg (0.4 mmol) of N,N'-carbonyldiimidazole was added and the mixture obtained was stirred at room temperature until the conversion of raw materials was complete. Then 75.9 mg (0.6 mmol) of dasatinib dissolved in DMF was added and the mixture was heated to reflux until the completion of the reaction, the solvent was evaporated under reduced pressure, the residue obtained was crystallized by using isopropanol to give 1.4 g of white solid (i.e. DSN-04).

$^{13}$C-NMR (75 MHz, DMSO-d6): 18.8, 25.8, 33.7, 41.3, 45.0, 51.3, 55.3, 58.2, 66-73, 84.2, 126.6, 127.3, 128.9, 129.7, 133.2, 133.9, 139.5, 141.3, 157.5, 157.8, 160.5, 162.4, 162.9, 165.6.

Example 5

The Antitumor Effect of Different Conjugates of Dasatinib with Polyethylene Glycol in Subcutaneous Tumor Model of K562 Human Chronic Myeloid Leukemia Experimental Method K562 cells were inoculated subcutaneously on the right back of NOD/SCID mice to establish human chronic myeloid leukemia subcutaneous xenograft animal model. When the mean tumor volume reached 130 mm$^3$, the mice used in the experiment were divided into groups and there were 8 mice in each group, then the mice were injected intravenously twice a week. The therapeutic efficiency was evaluated based on the relative tumor proliferation rate (T/C %).

Experimental Procedure (1) Cell Culture

K562 cell line was cultured in vitro in RPMI-1640 medium supplemented with fetal bovine serum with a volume ratio of 10% and L-glutamine (2 mM) at 37 with the air containing CO$_2$ with a proportion of 5%. The tumor cells were routinely passaged twice a week. The tumor cells in the exponential growth phase were collected and suspended in the mixture formed by PBS and matirgel with an equal volume, and then placed on ice for inoculation of tumor cells.

(2) Animal Grouping

5×10$^6$ of K562 cells were inoculated subcutaneously on the right back of the mice used in the experiment, the tumor growth was observed regularly, and stochastic grouping of the mice according to tumor size and body weight in mice and pharmacotherapy were carried out when the mean volume of the tumor reached 130 mm$^3$.

(3) Experimental Observation

In this study all the operations related to operating, nursing and treatment were undertaken according to the handbook approved by Association for Assessment and Accreditation of Laboratory Animal Care (AAALAC). After inoculation, animals were observed for morbidity and mortality every day. In everyday observation, the influence of tumor growth on animal normal behaviors (such as exercise, eating, drinking, change of weight, eyes, hair) and any other abnormalities were noticed. Death and clinical symptoms of animals in each group were recorded.

(4) Results Decision

Throughout the experiment, the weight and tumor size of mice were measured twice a week. The computational formula of tumor size was as follows: tumor volume (mm$^3$) =0.5×(long diameter of tumor x short diameter of tumor$^2$). According to the tumor size in experimental groups and control group, RTV and T/C ratio were calculated. RTV is the relative tumor volume. T/C ratio is the percentage ratio of relative tumor volumes in the treatment group and the control group at a time point after finish of treatment, and reflects the antitumor pharmacodynamic actions of the different treatment groups.

(5) Statistical Analysis

All the experimental results were represented by mean tumor volume±SE (standard error), in the process of statistical analysis, an unequal variances of relative tumor volume data was obtained, one-way analysis of variance (one-way ANOVA) and Dunnett T3 multiple comparison method for comparison of significant difference of the relative tumor volumes between groups were adopted, the p values less than 0.05 indicated that the difference was significant.

Experimental Results

The results of tumor growth in each treatment group and solvent control group are shown in Table 1 and Table 2.

TABLE 1

The T/C % values of tumor volume in each treatment group (5 mg/kg) (compared with the solvent control group)

| | The 14$^{th}$ day after grouping | | | |
| Experimental groups | Tumor volume ($\bar{x}$ ± SE) | Relative tumor volume ($\bar{x}$ ± SE) | T/C (%) | P value |
| --- | --- | --- | --- | --- |
| Group 1 solvent | 2447 ± 329 | 1819.4 ± 120.2 | — | — |
| Group 2 dasatinib | 311 ± 55 | 226.9 ± 30.0 | 12.4 | <0.001 |
| Group 3 DSN-1 | 349 ± 76 | 254.6 ± 42.2 | 14 | <0.001 |
| Group 4 DSN-2 | 372 ± 80 | 282.1 ± 46.3 | 16 | <0.001 |
| Group 5 DSN-3 | 295 ± 68 | 215.4 ± 41.1 | 11.8 | <0.001 |
| Group 6 DSN-4 | 210 ± 47 | 155.5 ± 28.5 | 8.5 | <0.001 |

TABLE 2

The T/C % values of tumor volume in each treatment group (5 mg/kg) (compared with the group using dasatinib)

| | The 21$^{st}$ day after grouping | | | |
| Experimental groups | Tumor volume ($\bar{x}$ ± SE) | Relative tumor volume ($\bar{x}$ ± SE) | T/C (%) | P value |
| --- | --- | --- | --- | --- |
| Group 2 dasatinib | 391 ± 79 | 289.1 ± 46.9 | — | — |
| Group 3 DSN-1 | 375 ± 89 | 277.5 ± 32.2 | 96 | 0.07 |
| Group 4 DSN-2 | 462 ± 114 | 350.3 ± 71.9 | 121 | 0.117 |
| Group 5 DSN-3 | 281 ± 56 | 208 ± 37.6 | 42 | <0.001 |
| Group 6 DSN-4 | 219 ± 45 | 161.8 ± 18.9 | 36 | <0.001 |

K562 human chronic myeloid leukemia subcutaneous tumor model had a rapid tumor growth rate, and the solvent control group ended on the 14$^{th}$ day after group therapy because of a mean tumor volume (2447 mm$^3$) more than 2000 mm$^3$. On the 14$^{th}$ day after group therapy, there was a statistically significant difference (p<0.001) between the efficacy in the solvent control group and that in the group using positive drug dasatinib (5 mg/kg) which had a mean tumor volume of 311 mm$^3$ and a relative tumor proliferation rate (T/C %) of 12.4%; and there was a statistically significant difference (p<0.001) between the efficacy in the solvent control group and that in the group using test drug DSN-4 (5 mg/kg) which had a tumor volume of 210 mm³ and a relative tumor proliferation rate (T/C %) of 8.5%; and there were statistically significant differences (with all the p values less than 0.001) between the efficacy in the solvent control group and that in the groups using test drugs DSN-1, DSN-2 and DSN-3 (5 mg/kg), respectively, which had respective mean tumor volumes of 349 mm³, 372 mm³ and 295 mm³ and respective relative tumor proliferation rates (T/C %) of 14%, 16%, and 11.8%.

On the 21$^{st}$ day after group therapy, there were statistically significant differences (p<0.001) between the efficacy in the group using dasatinib (5 mg/kg) with a mean tumor volume of 391 mm³ and that in the groups using the test drugs DSN-3 and DSN-4 (5 mg/kg), respectively, which had respective mean tumor volumes of 281 mm³ and 219 mm³ and respective relative tumor proliferation rates (T/C %) of 72% and 56%; there were no statistically significant differences (with all the p values more than 0.05) between the efficacy in the group using dasatinib (5 mg/kg) and that in the groups using the test drugs DSN-1 and DSN-2 (5 mg/kg), respectively, which had respective mean tumor volumes of 375 mm³ and 462 mm³ and respective relative tumor proliferation rates (T/C %) of 96% and 121%.

Compared with the solvent control group, the respective relative tumor proliferation rates (T/C %) of the groups using positive drug dasatinib (5 mg/kg), the test drugs DSN-1, DSN-2, DSN-3 and DSN-4 (5 mg/kg) were 12.4%, 14%, 16%, 11.8% and 8.5%, suggesting that all of the compounds had statistically significant effect of anti-K562 tumor growth (with p values less than 0.001), and compared with dasatinib (5mg/kg), the anti-tumor effect of the same dose of DSN-3 and DSN-4 (5 mg/kg) was more significant (with all the p values less than 0.001). Example 6: The pharmacodynamics research of different conjugates of dasatinib with polyethylene glycol in subcutaneous tumor model of PC-3 human prostate cancer Experimental Method PC-3 cells were inoculated subcutaneously on the right back of Balb/c nude mice to establish human prostate cancer subcutaneous xenograft animal model. When the mean tumor volume reached 160 mm³, the mice used in the experiment were divided into groups and there were 8 mice in each group, the mice were injected intravenously twice a week. The therapeutic efficiency was evaluated based on the relative tumor proliferation rate (T/C %).

Experimental Procedure (1) Cell Culture

PC-3 cell line was cultured in vitro in Ham's F12K medium supplemented with fetal bovine serum with a volume ratio of 10% and L-glutamine (2 mM) at 37 with the air containing $CO_2$ with a proportion of 5%, the tumor cells were routinely passaged twice a week. The tumor cells in the exponential growth phase were collected and suspended in the mixture formed by PBS and matirgel with an equal volume, and then placed on ice for inoculation of tumor cells.

(2) Animal Grouping $5 \times 10^6$ of PC-3 cells were inoculated subcutaneously on the right back of the mice used in the experiment, the tumor growth weas observed regularly, and stochastic grouping of the mice according to tumor size and body weight in mice and pharmacotherapy were carried out when the mean volume of the tumor reached 160 mm³.

(3) Experimental Observation

In this study all the operations related to operating, nursing and treatment were undertaken according to the handbook approved by Association for Assessment and Accreditation of Laboratory Animal Care (AAALAC). After inoculation, animals were observed for morbidity and mortality every day. In everyday observation, the influence of tumor growth on normal animal behaviors (such as exercise, eating, drinking, change of weight, eyes, hair) and any other abnormalities were noticed. Death and clinical symptoms of animals in each group were recorded.

(4) Results Decision

Throughout the experiment, the weight and tumor size of mice were measured twice a week. The computational formula of tumor size was as follows: tumor volume (mm³) =0.5×(long diameter of tumor×short diameter of tumor²). According to the tumor size in experimental groups and control group, RTV and T/C ratio were calculated. RTV is the relative tumor volume. T/C ratio is the percentage ratio of relative tumor volumes in the treatment groups and the control group at a time point after finish of treatment, and reflects the antitumor pharmacodynamic actions of the different treatment groups. When the experiment was finished, the tumors were recorded by photographs in the following two ways: 1. the animals in each group were euthanized by $CO_2$, and the tumor-bearing sides were placed upwards and taken photographs for recording by group; 2. the tumors were removed and weighed first, and T/C values (percentage ratio of tumor weights in treatment groups and the control group) were calculated, and then tumors in each group were placed in order at the same time and taken photographs for recording.

(5) Statistical Analysis

All the experimental results were represented by mean tumor volume±SE (standard error), in the process of statistical analysis, one-way analysis of variance (one-way ANOVA) and Dunnett T3 multiple comparison method for comparison of significant difference of the relative tumor volume between groups were adopted, the p values less than 0.05 indicated that the difference was significant.

Experimental Results

The results of tumor growth in each treatment group and solvent control group are shown in Table 3 and Table 4.

TABLE 3

The T/C % values of tumor volume in each treatment group (10 mg/kg) (compared with the solvent control group)

| | The 22$^{nd}$ day after grouping | | | |
| --- | --- | --- | --- | --- |
| Experimental groups | Tumor volume ($\bar{x}$ ± SE) | Relative tumor volume ($\bar{x}$ ± SE) | T/C (%) | P value |
| Group 1 solvent | 2462 ± 158 | 1572.6 ± 133.0 | — | — |
| Group 2 dasatinib | 1752 ± 76 | 1148.9 ± 112.7 | 73 | 0.002 |
| Group 3 DSN-1 | 1649 ± 142 | 1053.2 ± 107.4 | 67 | <0.001 |
| Group 4 DSN-2 | 1748 ± 146 | 1116.1 ± 98.2 | 71 | <0.001 |
| Group 5 DSN-3 | 1452 ± 139 | 927.5 ± 96.3 | 59 | <0.001 |
| Group 6 DSN-4 | 1182 ± 68 | 754.6 ± 84.5 | 48 | <0.001 |

TABLE 4

The T/C % values of tumor volume in each treatment group
(10 mg/kg) (compared with the group using dasatinib)

| | The 25th day after grouping | | | |
|---|---|---|---|---|
| Experimental groups | Tumor volume ($\bar{x} \pm SE$) | Relative tumor volume ($\bar{x} \pm SE$) | T/C (%) | P value |
| Group 2 dasatinib | 1868 ± 76 | 1235.3 ± 119.6 | — | — |
| Group 3 DSN-1 | 1476 ± 118 | 975.6 ± 103.5 | 79 | 0.030 |
| Group 4 DSN-2 | 1644 ± 146 | 1087.1 ± 88.2 | 88 | 0.296 |
| Group 5 DSN-3 | 1307 ± 155 | 864.7 ± 74.5 | 70 | 0.015 |
| Group 6 DSN-4 | 1177 ± 120 | 778.1 ± 82.4 | 63 | 0.001 |

PC-3 human prostate carcinoma subcutaneous tumor model had a rapid tumor growth rate and the body weight of the mice in the experiment decreased with the increasing of the tumor burden, and the solvent control group ended on the 22$^{nd}$ day after group therapy because of a mean tumor volume (2462 mm$^3$) more than 2000 mm$^3$. On the 22$^{nd}$ day after group therapy, there was a statistically significant difference (p<0.01) between the efficacy in the solvent control group and that in the group using positive drug dasatinib (10 mg/kg) which had a mean tumor volume of 1752 mm$^3$ and a relative tumor proliferation rate (T/C %) of 73%; and there was a statistically significant difference (p<0.001) between the efficacy in the solvent control group and that in the group using test drug DSN-4 (10 mg/kg) which had a tumor volume of 1182 mm$^3$ and a relative tumor proliferation rate (T/C %) of 48%; and there were statistically significant differences (with all the p values less than 0.001) between the efficacy in the solvent control group and that in the groups using test drugs DSN-1, DSN-2 and DSN-3 (10 mg/kg), respectively, which had respective average tumor volumes of 1649 mm$^3$, 1748 mm$^3$ and 1452 mm$^3$ and respective relative tumor proliferation rates (T/C %) of 67%, 71%, and 59%.

On the 25$^{th}$ day after group therapy, there were statistically significant differences (with p values less than 0.05, 0.05 and 0.01, respectively) between the efficacy in the group using dasatinib (10 mg/kg) with a mean tumor volume of 1868 mm$^3$ and that in the groups using the test drugs DSN-1, DSN-3 and DSN-4 (10 mg/kg) which had respective mean tumor volumes of 1476 mm$^3$, 1307 mm$^3$ and 1177 mm$^3$ and respective relative tumor proliferation rates (T/C %) of 79%, 70% and 63%; there was no statistically significant difference (p>0.05) between the efficacy in the group using dasatinib (10 mg/kg) and that in the group using the test drug DSN-2 (10 mg/kg) which had a mean tumor volumes of 1644 mm$^3$ and a relative tumor proliferation rates (T/C %) of 88%.

Compared with the solvent control group, the respective relative tumor proliferation rates (T/C %) of the groups using positive drug dasatinib (10 mg/kg), the test drugs DSN-1, DSN-2, DSN-3 and DSN-4 (10 mg/kg) were 73%, 67%, 71%, 59% and 48%, suggesting that all of the compounds had statistically significant effect of anti-PC-3 tumor growth (with all the p values less than 0.01), and compared with dasatinib (10 mg/kg), the anti-tumor effect of the same dose of DSN-1, DSN-3 and DSN-4 (10 mg/kg) was more significant (p<0.05).

The invention claimed is:

1. A dasatinib and nonlinear configuration polyethylene glycol conjugate shown as formula I

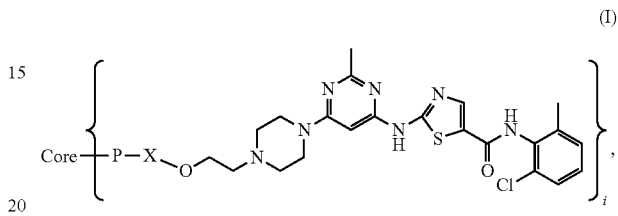

wherein Core is the core structure of the nonlinear configuration of polyethylene glycol, selected from residues of pentaerythritol, methylglucoside, sucrose, diethylene glycol, propanediol, glycerol or polyglycerol removed the hydrogen atom from the hydroxyl group; P is a polyethylene glycol residue with a number-average molecular weight of 300-60000 Da; X is selected from single bond, —CH$_2$CO—, —CH$_2$CH$_2$OCO— or —CH$_2$CH$_2$NHCO—; and i is selected from 3, 4, 6 or 8.

2. The conjugate of claim 1, wherein the said conjugate is shown as formula II:

(II)

n is an integer in a range of 30-200; X is selected from single bond, —CH$_2$CO—, —CH$_2$CH$_2$OCO— or —CH$_2$CH$_2$NHCO—; D is a dasatinib residue shown as structure III:

(III)

3. The conjugate of claim 2, wherein the said conjugate is shown as formula IV:

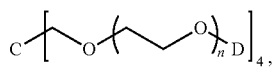

n is an integer in a range of 30-200.

4. The conjugate of claim 2, wherein the said conjugate is shown as formula V:

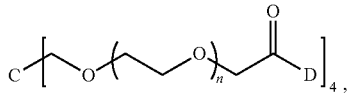

n is an integer in a range of 30-200.

5. The conjugate of claim 2, wherein the said conjugate is shown as formula VI:

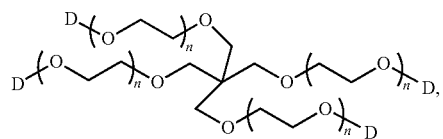

n is an integer in a range of 30-200.

6. The conjugate of claim 2, wherein the said conjugate is shown as formula VII:

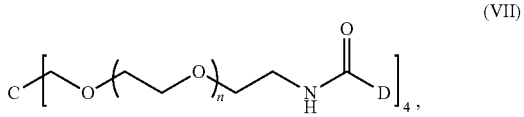

n is an integer in a range of 30-200.

7. The conjugate of claim 2, wherein the nonlinear configuration polyethylene glycol has a number-average molecular weight of 5000-40000 Da and four branches.

8. The conjugate of claim 2, wherein the nonlinear configuration polyethylene glycol described above has a number-average molecular weight of 20000 Da and four branches.

9. The conjugate of claim 2, wherein the said conjugate is selected from the group as shown in formula VIII to formula XI:

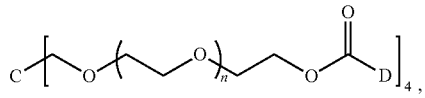

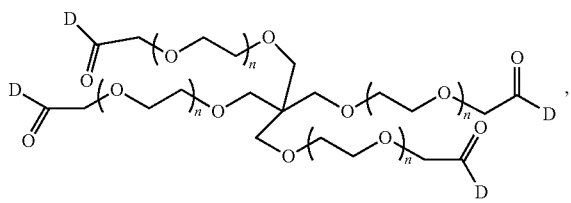

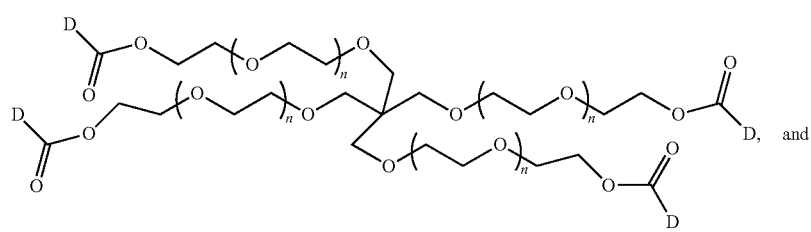

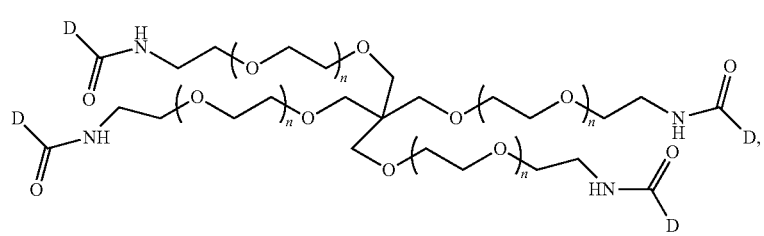

n in formula VIII to formula XI is an integer in a range of 30-200.

10. A pharmaceutical composition comprising the conjugate of claim 1 and pharmaceutically acceptable carriers or excipients.

11. The pharmaceutical composition of claim 10, wherein the said pharmaceutical composition are tablets, capsules, pills, granules, powders, suppositories, injections, solutions, suspensions, ointments, patches, lotions, drops, linimentums, sprays or other dosage forms.

12. The use of dasatinib and nonlinear configuration polyethylene glycol conjugate of claim 1 in the preparation of antitumor drugs.

* * * * *